United States Patent [19]
Knolle, Jr.

[11] Patent Number: 4,588,405
[45] Date of Patent: May 13, 1986

[54] INTRAOCULAR LENS ASSEMBLY
[75] Inventor: Guy E. Knolle, Jr., Houston, Tex.
[73] Assignee: American Hospital Supply Corporation, Evanston, Ill.
[21] Appl. No.: 503,278
[22] Filed: Jun. 10, 1983
[51] Int. Cl.[4] .................................................. A61F 2/16
[52] U.S. Cl. ...................................................... 623/6
[58] Field of Search ............................... 3/13, 1; 623/6
[56] References Cited

U.S. PATENT DOCUMENTS

| | | | |
|---|---|---|---|
| 4,110,848 | 9/1978 | Jensen | 3/13 |
| 4,159,546 | 7/1982 | Shearing | 3/13 |
| 4,174,543 | 11/1979 | Kelman | 3/13 |
| 4,203,168 | 5/1980 | Rainin et al. | 3/13 |
| 4,257,130 | 3/1981 | Bayers | 3/13 |
| 4,270,230 | 6/1981 | Poler | 3/13 |
| 4,304,012 | 12/1981 | Richard | 3/13 |
| 4,316,291 | 2/1982 | Severin | 3/13 |
| 4,316,292 | 2/1982 | Alexeev | 3/13 |
| 4,316,293 | 2/1982 | Bayers | 3/13 |
| 4,328,595 | 5/1982 | Sheets | 3/13 |
| 4,340,979 | 7/1982 | Kelman | 3/13 |
| 4,342,123 | 8/1982 | Gimbel | 3/13 |
| 4,418,431 | 12/1983 | Feaster | 3/13 |
| 4,437,194 | 3/1984 | Hahs | 3/13 |

FOREIGN PATENT DOCUMENTS 0032835 7/1981 European Pat. Off. ............ 3/13

OTHER PUBLICATIONS

Intermedics Intraocular Lenses (advertisement brochure), Intermedics Intraocular Inc. P.O. Box 70670, Pasadena, CA 91107, Models 034B and 034D, Apr. 1982.

Intraocular Lens Implantation Techniques & Complications (book), by Clayman, Jaffe, Galin, The C. V. Mosby Company (publisher) St. Louis, Toronto, London, 1983, pp. 152–155.

Brochure of American Medical Optics, printed 4/82.

Primary Examiner—Ronald L. Frinks
Attorney, Agent, or Firm—Gordon L. Peterson

[57] ABSTRACT

An intraocular lens assembly for implantation in the eye comprising a lens and first and second support members coupled to the lens and extending to locations spaced radially outwardly of the lens. At least one of the support members comprises a resiliently deformable strand having an outer segment which extends from the lens to a distal location spaced radially outwardly of the lens and an inner segment joined to the outer segment adjacent the distal location and extending to the lens. Major portions of the outer and inner segments are generally parallel, and regions of the parallel portions are curved so that the support member can be easily resiliently deformed toward the lens.

16 Claims, 6 Drawing Figures

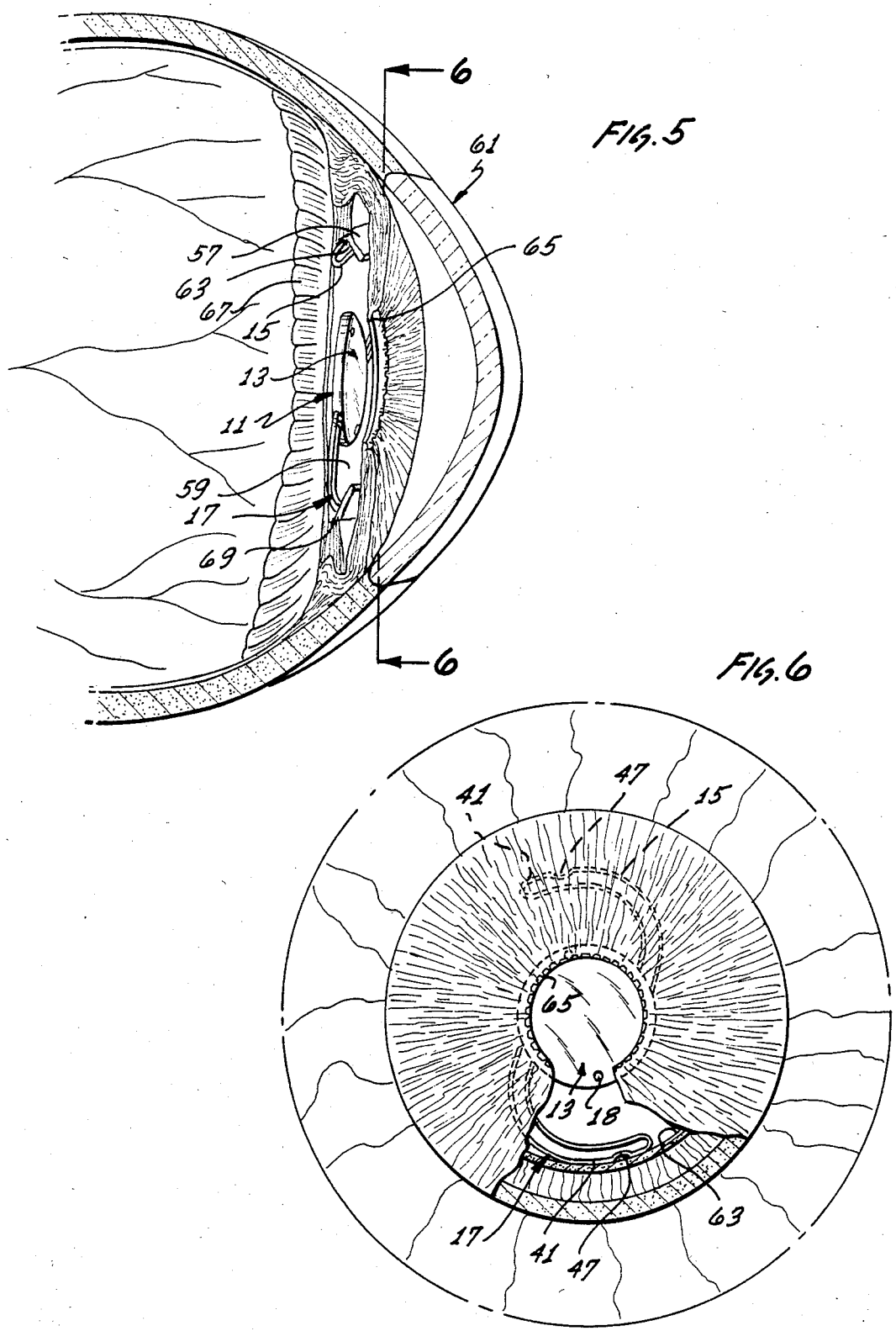

INTRAOCULAR LENS ASSEMBLY

BACKGROUND OF THE INVENTION

In cataract surgery, the natural lens is removed. To refocus the light on the retina and thus restore vision, an intraocular lens assembly can be implanted in place of the natural lens.

Intraocular lens assemblies can be implanted at various locations within the eye, such as within the anterior chamber or within the posterior chamber. Although an intraocular lens assembly is ostensibly of very simple construction, there is a wide variety of problems which has caused substantial study to be done in this field. As a result, a large number of intraocular lens assemblies have been proposed.

An intraocular lens assembly comprises a lens and structure to retain and support the lens within the eye. The retaining and supporting structure may include at least two support members, which are often referred to as loops. Each of the support members typically comprises an elongated strand which is resiliently deformable to facilitate insertion of the assembly to its desired location within the eye. When implanted, the strand resiliently bears against an adjacent surface of the eye to retain and position the lens.

One form of support member comprises a strand having one end affixed to the lens and its other end terminating at a location spaced radially of the lens. Such a construction is shown by way of example in Shearing U.S. Pat. No. 4,159,546. Implantation of an intraocular lens assembly of this kind requires resilient deformation of the free end of the strand radially inwardly toward the lens. If the strand and the lens are not precisely aligned in the same radial plane, the radial inward compression of the strand can act to move the lens axially out of the radial plane to impede the implantation process.

In another form of support member, both ends of the strand are attached to the lens, and a region of the strand intermediate its ends lies radially outwardly of the lens to support the lens in the implanted condition. One such construction is shown in Sheets U.S. Pat. No. 4,328,595. This construction tends to solve the problem of the lens moving axially in response to radial movement of the support member. However, this double-strand patented construction is somewhat difficult to compress radially. In addition, only point or narrow region contact is obtained with the surface of the eye which it engages in the implanted condition, and this increases unit loading on the eye and makes it difficult for the surgeon to rotate the lens assembly within the eye during implantation.

It is also known to provide intraocular lens assemblies which can be supported by hangers or clips rather than by using resilient elements acting against various eye surfaces, such as the posterior bag. One such device is shown in Rainin U.S. Pat. No. 4,203,168 which provides an anchor which extends through the iris. Constructions of this type are quite different from those which utilize the resilience of one or more support members to retain and position the lens assembly and are not suited for use in the capsular bag.

SUMMARY OF THE INVENTION

This invention provides an intraocular lens assembly which generally overcomes the above-noted problems with the prior art. The lens assembly of this invention is particularly adapted for mounting within the capsular bag of the posterior chamber following extracapsular removal of the natural lens. However, the lens assembly of this invention can be used in any location where the resilience of the support members can be used to support and position the lens. Thus, the lens assembly can be used in the posterior chamber following intracapsular removal of the natural lens and bag.

The intraocular lens assembly includes a lens and support means for supporting the lens in the implanted condition. The support means may include first and second support members coupled to the lens and extending to locations spaced radially outwardly of the lens. At least one of the support members comprises a resiliently deformable strand having an outer segment which extends from a first location adjacent the periphery of the lens to a distal location spaced radially outwardly of the lens and an inner segment joined to the outer segment adjacent the distal location and extending to a second location adjacent the periphery of the lens. Thus, both ends of the strand are coupled to the lens to give the lens assembly added rigidity against movement of the lens axially in response to radial compression of the support member. Although the distal location referred to above is spaced radially outwardly of the lens, it may of may not be offset axially of the lens.

Although some rigidity in a direction axially of the lens is desired, at least one of the support members should have substantial resilient flexibility in the radial direction. To accomplish this with a two-segment support member, at least major portions of the outer and inner segments are generally parallel, and at least regions of such major portions of the segments are curved. These two factors combine to provide the desired radial flexibility without sacrificing the desired axial stiffness and to assure that both the inner and outer segments will deflect similarly and compatibly.

Of course, the outer and inner segments need not be perfectly parallel as some convergence, divergence and irregularities in their configurations can be accepted without degrading the performance of the lens assembly. However, the inner and outer segments should not be configured so as to be totally dissimilar. Viewed from another perspective, the outer and inner segments are preferably similar in a geometric sense.

For optimum results, substantially the full lengths of the outer and inner segments are generally parallel, and the length of the inner segment between the lens and its distal end is only slightly less than the length of the outer segment between the lens and its distal end. This makes the bending characteristics of the two segments more nearly equal. Also, the two locations at which the segments emerge from the lens and the two segments themselves are preferably closely adjacent.

The strand should be very flexible but it must have memory. Accordingly, the strand can be described as resiliently or elastically deformable in that it can be deformed but, once the deforming force is removed, it returns to its original unstressed condition.

The distal regions of the outer segment are configured to provide a long length of surface contact with the surface within the eye which it contacts when the intraocular lens assembly is implanted. This reduces unit loading on the eye. This can be accomplished by imparting to the outer segment an appropriate curvature. This roundness of the outer segment also facilitates rotation of the lens assembly by the surgeon during implantation.

In a preferred construction, the outer segment has proximal and distal curves, with the proximal curve being sharper than the distal curve and with both of the curves being concave toward the lens. The proximal curve is provided primarily to help provide the proper resilient flexing movement of the support member toward and away from the lens. The distal curve is provided to impart the desired roundness to the outer segment to maximize the length of contact with the adjacent structure of the eye and to facilitate rotation of the lens assembly by the surgeon as described above.

Prior to insertion of the lens assembly into the eye, the resilient support member should be deflected radially inwardly and retained in this compressed position during the initial phases of implantation. The proximal and distal curves provide a desired roundness to the loop in the compressed position which facilitates insertion of the lens assembly. To facilitate the deflection and retention of the support member, the outer or inner segment can be deformed to define an outwardly opening notch. This notch is adapted to receive a lug of an appropriate tool, such as forceps, to deflect the support member to the compressed position and to retain it in the compressed position during implantation. The notch is preferably located in the distal curve.

Although one or more of the support members can be provided, two generally oppositely located support members are preferred. Although the support members preferably lie in the same generally radial plane, this is not essential. The support members may be of identical or different constructions, and the strand of the support member may be integrally coupled to the lens, i.e., the strand and lens may be constructed from one piece of material, or constructed from separate elements and coupled to the lens.

The invention, together with additional features and advantages thereof, may best be understood by reference to the following description taken in connection with the accompanying illustrative drawing.

BRIEF DESCRIPTION OF THE DRAWING

FIG. 5 is a fragmentary, pictorial sectional view of the human eye having the lens assembly of this invention implanted in it.

FIG. 6 is a sectional view taken generally along line 6—6 of FIG. 5.

DESCRIPTION OF THE PREFERRED EMBODIMENT

Figure 1:
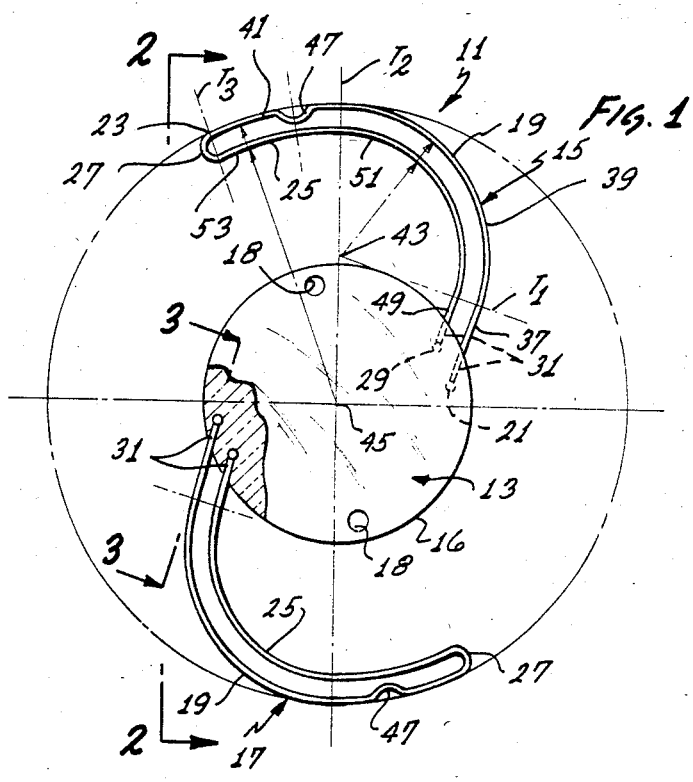
FIG. 1 is a front elevational view partially in section of an intraocular lens assembly constructed in accordance with the teachings of this invention.
Figure 2:
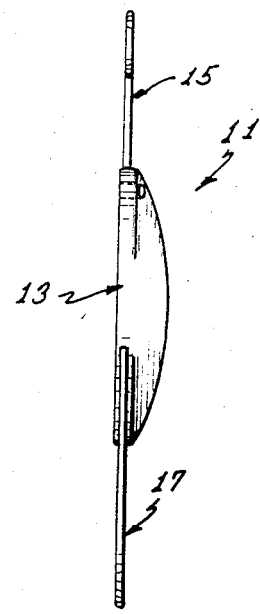
FIG. 2 is a side elevational view of the lens assembly.

FIGS. 1 and 2 show an intraocular lens assembly 11 which comprises a lens 13 and support members in the form of loops 15 and 17. The lens 13 is adapted to replace the natural lens of the human eye and may be, for example, a planoconvex lens of suitable diopter power having a circular periphery 16 and diametrically opposed rotation apertures 18. The lens 13 may be formed by a precision machining and polishing process in which the periphery 16 of the lens is rounded and polished. Conventional biocompatible materials, such as the clinical quality of polymethylmethacrylate, may be used for the lens 13.

In the embodiment illustrated, the loops 15 and 17 are identical, and corresponding parts are designated by corresponding reference numerals. The loop 15 comprises an integral, flexible, resilient strand having an outer segment 19 extending from one end 21 through the periphery 16 at one location to a distal location 23 spaced radially outwardly of the lens 13 and an inner segment 25 joined to the outer segment by a connecting segment 27 adjacent the distal location 23 and extending through the periphery 16 at a second location to a second end 29 of the strand.

The strand is very fine and may have, for example, a circular cross section with a 0.006 inch or greater diameter. The strand is constructed of a suitable biocompatible material, such as polypropylene. Although the strand may comprise multiple filaments, in the illustrated embodiment, it includes only a single filament.

Figure 3:
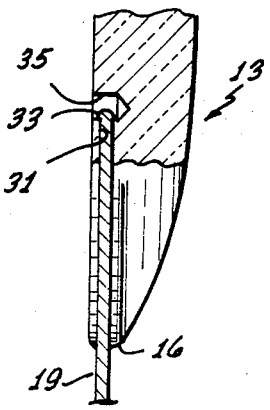
FIG. 3 is an enlarged fragmentary sectional view taken generally along line 3—3 of FIG. 1.

The ends 21 and 29 of the loop 15 are suitably coupled to the lens 13 in any suitable manner. In the embodiment illustrated, the end portions of the loop 15 are inserted into parallel closely adjacent passages 31 (FIGS. 1 and 3) in the lens 13 and retained therein by enlargements 33 (FIG. 3) in blind bores 35 which intersect the passages 31, respectively. The enlargements 33 can be formed, for example, by heating the ends of the loop 15 with a hot rod inserted into the blind bores 35. When so mounted, the loops 15 and 17, in the embodiment illustrated, lie in the same radial plane with the lens 13 as shown in FIG. 2 and are spaced radially outwardly of the lens.

More specifically, the outer segment 19 comprises a straight section 37, a proximal curve 39 which extends for over ninety degrees, and a distal curve 41 which is not nearly as sharp as the proximal curve 39. Although various constructions are possible, the curves 39 and 41 have centers 43 and 45, respectively, with the center 45 being at the center of the lens 13 and with the center 43 being near the periphery 16 of the lens 13 at the twelve o'clock position as viewed in FIG. 1. Thus, the proximal curve 39 has a shorter radius than the distal curve 41, and both of these curves are concave toward the lens 13. A region of the distal curve 41 is deformed radially inwardly toward the lens 13 to define a notch 47 which opens outwardly.

The inner segment 25 also has a straight section 49, a proximal curve 51 and a distal curve 53 with the distal curves 41 and 53 being integrally joined by the connecting segment 27. The center of curvature of the proximal curve 51 and the distal curve 53 are the centers 43 and 45, respectively. Thus, the proximal curves 39 and 51 are parallel, concentric and geometrically similar, and except for the notch 47, the distal curves 41 and 53 are also parallel and geometrically similar. The straight sections 37 and 49 are parallel. The points of tangency amont the curves and sections of the segments 19 and 25 are shown in FIG. 1 by reference lines $T_1$ and $T_2$, and the points of tangency between the segments 19, 25 and 27 are shown by reference line $T_3$.

The segments 19 and 25 are closely adjacent, and the segment 25 is between the segment 19 and the lens 13. The segments 19 and 25 of the loops 15 and 17 emerge from the periphery 16 of the lens 13 at diametrically opposed regions of the lens and curve counterclockwise, although the loops could curve clockwise, if desired. The exposed length of the inner segment 25 is only slightly less than the exposed length of the outer segment.

The loops 15 and 17 are resiliently deformable in a direction radially of the lens 13. However, because each of the loops 15 and 17 comprises an outer segment 19 and an inner segment 25 and both ends 21 and 29 of the loops are affixed to the lens, the lens assembly 11 is relatively stiff in a direction axially of the lens 13. Accordingly, radial flexure of one or both of the loops 15 and 17 will not provide an axial component of force, even with some radial misalignment between the loops and the lens 13, which is likely to be sufficient to impart significant axial movement to the lens.

Although the loops 15 and 17 can be moved radially toward the lens 13 in any desired manner, this can be most conveniently accomplished with any tool, such as a forceps (not shown) which has a lug 55 which can be received in the notch 47. The lug 55 and the notch 47 interlock to facilitate radial inward movement of the loop 15 to a position in which it contacts the periphery of the lens 13. This interlock also facilitates retention of the loop 15 in that position during implantation of the lens assembly 11. Although the loop 17 can be similarly moved radially inwardly, it is ordinarily necessary to move only one of the loops 15 and 17 radially inwardly prior to implantation.

FIGS. 5 and 6 show the intraocular lens assembly 11 implanted in the capsular bag 57 in the posterior chamber 59 of a human eye 61. In this regard, the natural lens has been previously removed leaving the bag 57 in position within the posterior chamber 59.

Figure 4:
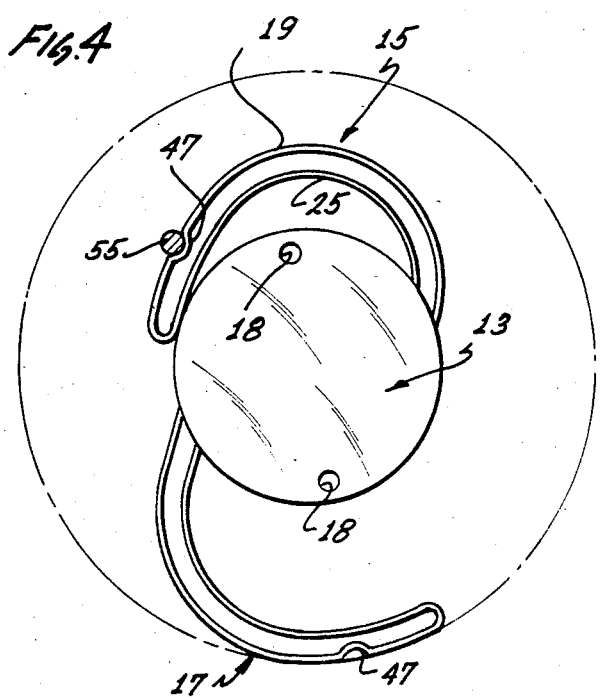
FIG. 4 is a front elevational view similar to FIG. 1 with one of the support members deflected radially toward the lens.

The lens assembly 11 can be implanted in the bag 57 using known surgical techniques. These techniques include flexing of the loop 15 radially inwardly to the position shown in FIG. 4, and with the lens assembly of this invention, this can be more easily accomplished utilizing a tool having the lug 55 which can be received within the notch 47 as shown in FIG. 4. The lens assembly 11 is inserted into the bag 57, and the restraint of the loop 15 provided by the lug 55 is then removed to allow resilient extension of the loop 15 to the position shown in FIGS. 5 and 6.

As shown in FIGS. 5 and 6, the bag 57 has an equatorial zone 63 which is roughly circular and against which outer regions, and in particular, the distal curves 41 can bear. The curvature of the distal curves 41 approximates the curvature of the equatorial zone 63 such that a long area of contact is achieved between the equatorial zone and the loops with such zone of contact being interrupted only by the relatively small notches 47. This long zone of contact reduces unit loading on the bag 57 and, because the curvature of the distal curves 41 approximates the curvature of the equatorial zone 63, the surgeon can rotate the lens assembly 11 in the bag 57 by engaging an appropriate tool (not shown) in the apertures 18 of the lens 13.

The loops 15 and 17 support the lens assembly 11 in the bag 57 and position the lens 13. As shown in FIGS. 5 and 6, the lens 13 is essentially coaxial with the iris 65, which is located posteriorly of the cornea, and is located anteriorly of the posterior wall 67. The ciliary body 69 is not contacted by the loops 15 and 17.

Although an exemplary embodiment of the invention has been shown and described, many changes, modifications and substitutions may be made by one having ordinary skill in the art without necessarily departing from the spirit and scope of this invention.

I claim:

1. An intraocular lens assembly for implantation in the eye comprising:

a lens;

support means for supporting said lens, said support means being coupled to said lens and extending to locations spaced radially outwardly of the lens;

said support means comprising at least one support member which includes a resiliently deformable strand having an outer segment which extends from a first location adjacent the periphery of the lens to a distal location spaced radially outwardly of the lens and an inner segment joined to the outer segment adjacent the distal location and extending to a second location adjacent the periphery of the lens;

at least regions of said inner segment being generally between the outer segment and the lens; and the outer and inner segments being generally parallel throughout substantially their full lengths and regions of the outer and inner segments being curved whereby said support member can be resiliently deformed to bring said distal location toward the lens.

2. An intraocular lens assembly as defined in claim 1 wherein said first and second locations are closely adjacent.

3. An intraocular lens assembly as defined in claim 2 wherein a region of said outer or inner segment is deformed to define an outwardly opening notch.

4. An intraocular lens assembly as defined in claim 1 wherein a region of said outer or inner segment is deformed to define an outwardly opening notch.

5. An intraocular lens assembly as defined in claim 1 wherein said strand includes a relatively short connecting segment for joining the inner segment to said outer segment at said distal location.

6. An intraocular lens assembly as defined in claim 1 wherein a distal region of said outer segment is configured to provide a long length of surface contact with the surface within the eye which it contacts when the intraocular lens assembly is implanted.

7. An intraocular lens assembly as defined in claim 1 wherein each of said outer and inner segments has proximal and distal curves with each of the proximal curves being sharper than the assoicated distal curve and with said curves being concave toward the lens.

8. An intraocular lens assembly as defined in claim 1 wherein each of said regions comprises a curve which extends for at least about ninety degrees.

9. An intraocular lens assembly as defined in claim 1 wherein said support means includes a second support member and said one support member and said second support member lie essentially in the same plane and said second support member is coupled to said lens at a region of said lens generally diametrically opposite said first and second locations.

10. An intraocular lens assembly as defined in claim 1 wherein said support means includes a second support member which comprises a resiliently deformable strand having an outer segment which extends from a third location adjacent the periphery of the lens to a distal location spaced radially outwardly of the lens and an inner segment joined to the outer segment of the second support member adjacent said distal location of the second support member and extending to a fourth location adjacent the periphery of the lens, said first and second locations being at a first region and said third and fourth locations being at a second region, and said first and second regions being generally diametrically opposed.

11. An intraocular lens assembly as defined in claim 2 wherein each of said segments has proximal and distal curves with the proximal curve being sharper than the distal curve and with said curves being concave toward the lens, said strand includes a connecting segment for joining the inner segment to the outer segment at said distal location, and at least a portion of the distal curve of said outer segment is configured to provide a long length of surface contact with the surface within the eye which it contacts when the intraocular lens is implanted.

12. An intraocular lens assembly as defined in claim 11 wherein said outer or inner segment is deformed at a region of said distal curve to define an outwardly opening notch which is adapted to receive a lug of a tool usable to resiliently deform the first support member radially inwardly toward the lens.

13. An intraocular lens assembly for implantation in the eye comprising:
   a lens;
   first and second support members coupled to said lens and extending to locations spaced radially outwardly of the lens;
   at least one of said support members comprising a resiliently deformable strand having an outer segment which extends from the lens to a distal location spaced radially outwardly of the lens and an inner segment joined to the outer segment adjacent said distal location and extending to the lens;
   regions of said inner segment being generally between the outer segment and the lens; and
   at least major portions of the outer and inner segments being geometrically similar and each of said segments including a straight section extending from the lens, a proximal curve joined to the straight section, and a distal curve with the proximal curve being sharper than the distal curve and with said curves being concave toward the lens whereby said one support member can be resiliently deformed to bring said distal location toward the lens.

14. An intraocular lens assembly as defined in claim 13 wherein substantially the full lengths of said outer and inner segments are geometrically similar.

15. An intraocular lens assembly as defined in claim 14 wherein the length of said inner segment from the lens to its distal end is only slightly less than the length of the outer segment between the lens and the distal location.

16. An intraocular lens assembly as defined in claim 13 wherein said proximal curves have approximately the same center and said distal curves have approximately the same center.

* * * * *